Oct. 13, 1942. W. I. JOHNSTON Plant Pat. 551
ROSE PLANT
Filed June 4, 1942
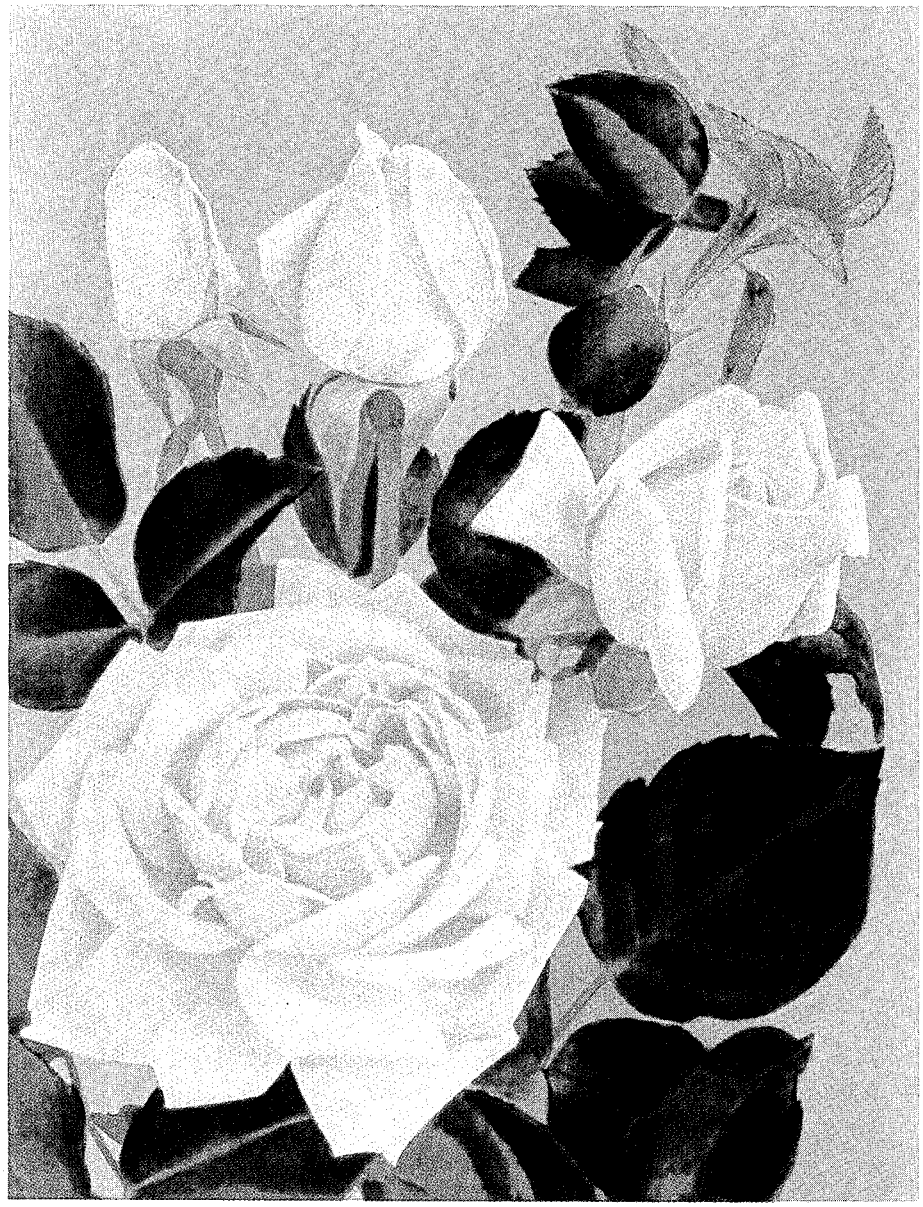
Inventor
W. I. Johnston
By Robb & Robb
Attorneys Patented Oct. 13, 1942

Plant Pat. 551

UNITED STATES PATENT OFFICE

551

ROSE PLANT

Walter Irwin Johnston, Portadown, Northern Ireland, assignor to Jackson & Perkins Company, Newark, N. Y.

Application June 4, 1942, Serial No. 445,767

1 Claim. (Cl. 47—61)

The present invention relates to a new and distinct variety of rose plant, originated by crossing an unnamed seedling and the variety "Le Progrés."

The primary distinctions of this new rose are found in its bud and flowers, namely, the globular shape of the buds and the habit of the petals to very symmetrically unfold in the different stages of development to maturity, and the unusual color combination (hereinafter specifically described) in the yellow range, creating a very soft effect not found in any other rose of which I am aware.

Furthermore, it may be noted, this new rose is of appealing interest because of its addition to the type of the old-fashioned globular roses as distinguished from the high centered roses now so popular.

Of secondary importance, this new variety is a low growing bush which is heavily covered with leathery Cress Green foliage, forming an attractive setting for the large and full petaled blossoms.

The following is a detail description of the new variety, color terminology being in accord with Ridgway's Color Standard:

Parentage: Seedling.

*Seed parent.*—Unnamed seedling.

*Pollen parent.*—"Le Progrés."

Classification: Botanic and commercial—hybrid tea.

*Flower*

(Observations made in the fields of Jackson & Perkins Company, Newark, New York, in the afternoon of September 22, 1941.)

Blooming habit: Recurrent—continuous.

Bud:

*Size.*—Large.

*Form.*—Globular. Is not affected by wet or hot weather.

*Color.*—When sepals first divide—Old Rose, Plate 13. When petals begin to unfurl—Apricot Yellow, Plate 4. When half blown: inside of petals—Straw Yellow, Plate 16, overcast with Lemon Chrome, Plate 4; reverse of petals—Straw Yellow, Plate 16, overlaid with Light Salmon Orange, Plate 2.

*Sepals.*—Slightly branched, "hood" above bud. Curl back when petals begin to unfurl. *Color*—Parrot Green, Plate 6, outside; Grass Green, Plate 31, inside.

*Calyx.*—*Shape*—*apple.* *Size*—*broad.* *Aspect*—Smooth. *Color*—Oil Green, Plate 5.

*Peduncle.*—*Length*—medium. *Aspect*—smooth. *Color*—Oil Green, Plate 5. *Strength*—erect; slender.

*Opening.*—Bud opens well. Is not affected by adverse conditions.

Bloom:

*Size.*—Large. Average size when fully expanded—four inches.

*Borne.*—Several together.

*Stems.*—Medium length; strong.

*Form.*—When first open—cupped and globular. *Permanence*—retains its form to the end.

*Petalage.*—Double (full but open center). Number of petals under normal conditions—45.

*Color.*—Center of flower—Capucine Orange, Plate 3. Outer petals—Empire Yellow, Plate 4. Base of petals (aiglet)—Lemon Chrome, Plate 4. Inside of petals—between Empire Yellow, Plate 4, and Pinard Yellow, Plate 4, as to each. Reverse of petals—Pinard Yellow, Plate 4, overcast with Light Salmon Orange, Plate 2. General tonality from a distance—Orange Buff, Plate 3.

*Discoloration.*—General tonality at end of first day—Capucine Orange, Plate 3. Second day—Orange Buff, Plate 3. Third day—Light Orange Yellow, Plate 3.

Petals:

*Texture.*—Leathery. Is not affected by wet or hot weather.

*Appearance.*—Inside—satiny. Outside—shiny.

*Form.*—Oval.

*Arrangement.*—Irregular. Petaloids in center—few; small.

*Persistence.*—Drop off cleanly.

*Fragrance.*—Moderate. *Nature*—fruity (Russet apple).

*Lasting quality.*—On the plant and as cut flower—long.

Genital organs:

*Stamens, anthers.*—Large; many. *Color*—Light Cadmium, Plate 4. *Arrangement*—regular around styles.

*Stamens, filaments (threads).*—Long. *Color*—Lemon Chrome, Plate 4.

*Pollen.*—Lemon Yellow, Plate 4.

*Styles.*—Bunched evenly; medium length; thin.

*Stigmas.*—Buff Yellow, Plate 4.

*Ovaries.*—All enclosed in calyx.

*Plant*

Form: Bush.
Growth: Vigorous; branching.
Foliage: 5 leaflets.
*Size*—Large.
*Quantity*—Abundant.
*Color.—New foliage:* Upper side—Vandyke Red, Plate 13; mid-rib Yellowish Oil Green, Plate 5; under side—Vandyke Red, Plate 13. *Old foliage:* Upper side—Cress Green, Plate 31; under side—Lite Cress Green, Plate 31.
*Shape.*—Oval pointed.
*Texture.*—Upper side—leathery. Under side—smooth. *Ribs and veins*—prominent.
*Edge.*—Serrated (saw toothed).
*Serration.*—Single; sharp.
*Rachis.—Color*—Jade Green, Plate 3. Under side—prickles.
*Stipules.*—Medium length; bearded.
*Disease resistance.*—Resistant, insofar as this is evidenced by absence of any disease throughout development and establishment of this variety.

Wood:
*New wood.—Color*—Cosse Brown, Plate 5. *Bark*—smooth.
*Old wood.—Color*—Elm Green, Plate 17. *Bark*—smooth.

Thorns (thorns are divided into thorns, prickles, and short needles):
*Thorns.*—On main stalks from base and on laterals from stalk—few. *Form*—narrow base; medium length; hooked downward. *Color when young*—Isabella Color, Plate 30. *Position*—irregular.
*Prickles.*—On main stalks and on laterals—few. *Color*—Honey Yellow, Plate 30.

I claim:

A new and distinct variety of rose plant, characterized as to novelty by low growing habit for a bush type of plant, the unusual color combination of the flowers, globular shape of the buds and symmetrical unfolding of the petals in the different stages of development to maturity, substantially as shown and described.

WALTER IRWIN JOHNSTON.